(12) United States Patent  (10) Patent No.: US 7,677,730 B2
Shimizu  (45) Date of Patent: Mar. 16, 2010

(54) OPHTHALMOLOGIC PHOTOGRAPHING APPARATUS

(75) Inventor: Satoshi Shimizu, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 78 days.

(21) Appl. No.: 12/032,972

(22) Filed: Feb. 18, 2008

(65) Prior Publication Data

US 2008/0212027 A1 Sep. 4, 2008

(30) Foreign Application Priority Data

Mar. 2, 2007 (JP) ............................. 2007-052596

(51) Int. Cl.
*A61B 3/14* (2006.01)
(52) U.S. Cl. ....................................... 351/206; 351/200
(58) Field of Classification Search ......... 351/205–206, 351/210
See application file for complete search history.

(56) References Cited

U.S. PATENT DOCUMENTS 6,142,629 A 11/2000 Adel et al.
7,048,379 B2 5/2006 Miller
2002/0013573 A1* 1/2002 Telfair et al. ................... 606/5
2005/0041207 A1* 2/2005 Miller et al. ................. 351/200
2007/0019160 A1 1/2007 Kleen

FOREIGN PATENT DOCUMENTS

JP 1-300927 A 12/1989
JP 2002-523167 A 7/2002
WO 2004/082465 9/2004
WO 2006/016366 2/2006

* cited by examiner

*Primary Examiner*—Joseph Martinez
*Assistant Examiner*—James R Greece
(74) *Attorney, Agent, or Firm*—Canon U.S.A., Inc. I.P. Division (57) ABSTRACT

An ophthalmologic photographing apparatus includes a light source having two or more types of light-emitting-diode (LED) light emitting elements configured to emit light of different wavelengths, an illumination optical system configured to illuminate a fundus of a subject's eye with light emitted by the light source, an imaging optical system configured to form a fundus image from light reflected from the fundus of the subject's eye illuminated by the illumination optical system, and a control unit configured to control the light source to emit light of different wavelengths, with which the fundus of the subject's eye is illuminated, between when the formed fundus image is observed and when the formed fundus image is captured as a still image.

3 Claims, 8 Drawing Sheets

FIG.14

OPHTHALMOLOGIC PHOTOGRAPHING APPARATUS

BACKGROUND OF THE INVENTION

1. Field of the Invention

The present invention relates to an ophthalmologic photographing apparatus for photographing a fundus of a subject's eye.

2. Description of the Related Art

Fundus cameras are roughly classified into non-mydriatic fundus cameras and mydriatic fundus cameras. The non-mydriatic fundus camera captures an image of a fundus of a subject's eye with visible light after the subject's eye is observed with near-infrared light. The mydriatic fundus camera captures an image of a fundus of a subject's eye with visible light after the subject's eye, whose pupil is dilated with a mydriatic, is observed with visible light.

In the mydriatic fundus camera, a visible light cut-off filter is inserted in front of a halogen light source in order to prevent a pupil of a subject's eye from being narrowed with observation light. Consequently, only an infrared component of light emitted from the halogen light source is transmitted by the visible light cut-off filter and is irradiated on a fundus of a subject's eye. When photographing a fundus of a subject's eye, the fundus is photographed with visible light by causing a xenon light source to emit light.

Japanese Patent No. 3,004,276 discusses a non-mydriatic fundus camera using a light source for both observation and photographing, which can emit two types of light, i.e., visible light and infrared light, in order to simplify the light source unit employed.

The fundus camera discussed in Japanese Patent No. 3,004,276 switches between photographing light, which is visible light, and illumination light, which is infrared light, by insertion and removal of wavelength selecting filters, such as a visible light cut-off filter and an infrared light cut-off filter, into and out of the optical path of an illumination optical system. Thus, the fundus camera selects a wavelength of light, which is transmitted by the cut-off filter inserted into the optical path. However, the fundus camera using two types of filters, i.e., a visible cut-off filter and an infrared light cut-off filter, has a drawback in that the optical system is complicated and is increased in size.

With recent increases in the intensity of light emitted from light-emitting-diodes (LEDs), fundus cameras using an LED light emitting element as an illumination light source have been proposed. However, the emission wavelength band and the intensity of light emitted from an LED light emitting element are limited. Thus, it is difficult to configure a fundus camera to use a light source for both observation and photographing and to switch between visible light and infrared light using wavelength selecting filters, as discussed in Japanese Patent No. 3,004,276. Thus, a separate illumination light source optical system and observation light source optical system are needed. Consequently, it is difficult to reduce the system in size.

SUMMARY OF THE INVENTION

The present invention is directed to an ophthalmologic photographing apparatus capable of efficiently and uniformly illuminating a fundus of a subject's eye with a simple structure using a single light source serving as both an observation light source and a photographing light source.

According to an aspect of the present invention, an ophthalmologic photographing apparatus includes a light source having one or more first light emitting elements configured to emit light and having one or more second light emitting elements configured to emit light having a different wavelength to the light emitted by the first light emitting elements, an illumination optical system configured to illuminate a fundus of a subject's eye with light emitted by the light source, an imaging optical system configured to form a fundus image from light reflected from the fundus of the subject's eye illuminated by the illumination optical system, and a control unit configured to control the light source so that the light emitted by the light source with which the fundus of the subject's eye is illuminated differs in wavelength between when the formed fundus image is observed without capturing the image and when the formed fundus image is captured as a still image.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DETAILED DESCRIPTION OF THE EMBODIMENTS

Various exemplary embodiments, features, and aspects of the invention will now be described in detail with reference to the drawings.

First Exemplary Embodiment

Figure 1:
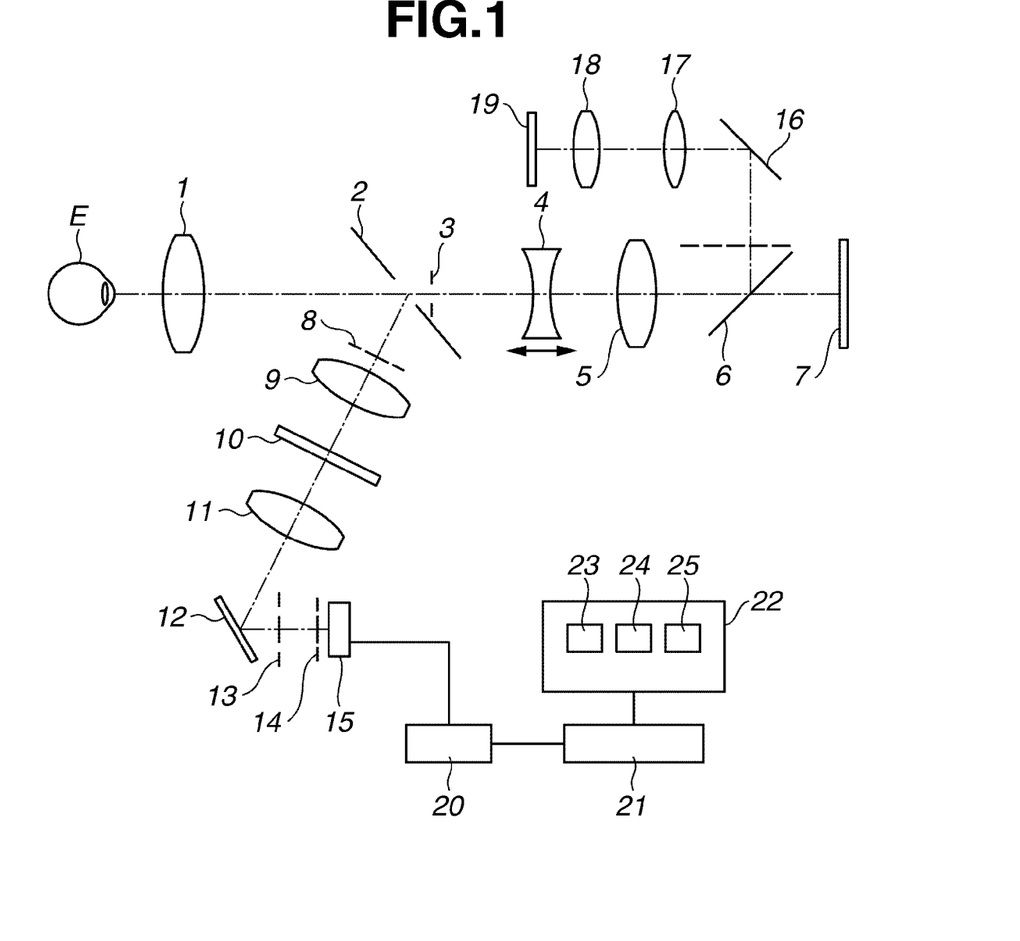
FIG. 1 illustrates a configuration of a non-mydriatic fundus camera according to a first exemplary embodiment of the present invention.

FIG. 1 illustrates a configuration of a non-mydriatic fundus camera according to a first exemplary embodiment of the present invention. An objective lens 1, a perforated mirror 2, a photographic aperture stop 3, a focus lens 4 that is movable along an optical axis, an imaging lens 5, a moveable (flip-up) mirror 6, and an imaging unit 7 are sequentially arranged in front of a subject's eye E and constitute a photographing optical system.

Figure 2:
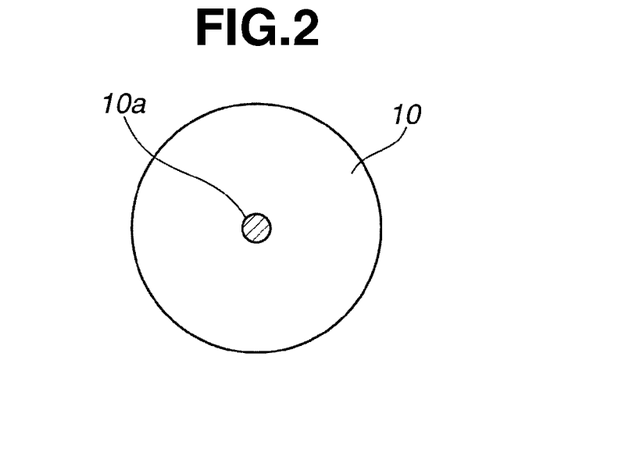
FIG. 2 is a front view illustrating an exemplary black point plate according to the first exemplary embodiment of the present invention.

A cornea stop 8, a relay lens 9, a black point plate 10, a further relay lens 11, and a mirror 12 configured to reflect illumination light are sequentially disposed in a light incident direction of the perforated mirror 2. The cornea stop 8 has a ring-shaped opening for separating observation illumination light from photographing illumination light so as to prevent the incidence of harmful reflection light on the photographic aperture stop 3, which is obtained by reflecting illumination light and comes from a cornea of the subject's eye E. The black point plate 10 is a glass plate having a small shield 10a, which is referred to as a black point, disposed at a position conjugate with the photographic stop 3, as illustrated in FIG. 2.

A crystalline lens stop 13 and a pupil stop 14, which has a ring-shaped opening disposed at a position which is optically substantially conjugate with that of the pupil of the subject's eye E, are disposed in an incident direction of the mirror 12 in order to separate an illuminating light flux from a photographing light flux, thereby preventing light reflected by a crystalline lens of the subject's eye E from being incident on the photographic stop 3. An LED illumination light source unit 15 for generating observation illumination light and photographing illumination light is disposed behind the pupil stop 14. Thus, an illumination optical system is constituted.

A reflection mirror 16, a field lens 17, a relay lens 18, and an image sensor 19, which is sensitive to near-infrared light, are sequentially disposed in a light reflecting direction of the flip-up mirror 6, and constitute an observation optical system.

The LED illumination light source unit 15 is connected to a control unit 21 via a power supply circuit 20. An operation panel 22 is connected to the control unit 21. An observation light amount adjusting knob 23, a photographing light amount adjusting knob 24, a photographing switch 25, and an indicator (not illustrated), which indicates a status, are provided on the operation panel 22.

The control unit 21 outputs a control signal to the power supply circuit 20 according to signals output from the observation light amount adjusting knob 23, the photographing light amount adjusting knob 24, and the photographing switch 25 so as to control lighting of the LED illumination light source unit 15.

Figure 3:
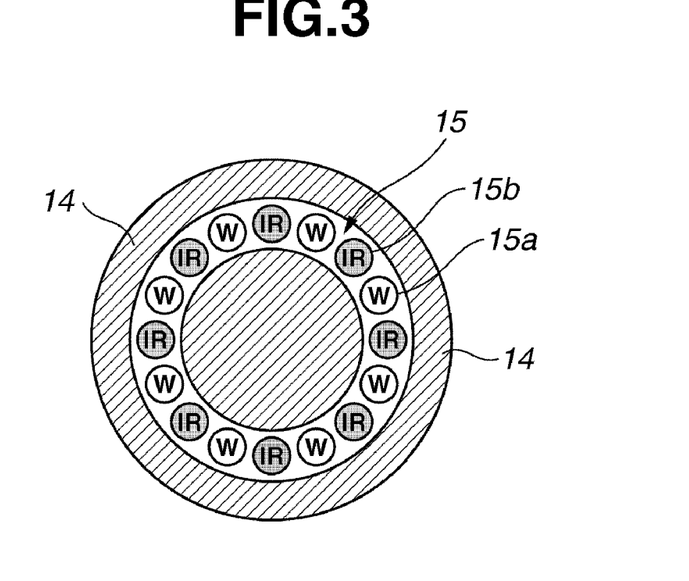
FIG. 3 illustrates an exemplary arrangement of LED light emitting elements according to the first exemplary embodiment of the present invention.

FIG. 3 illustrates an exemplary arrangement of LED light emitting elements provided in the LED illumination light source unit 15. As illustrated in FIG. 3, the LED illumination light source unit 15 includes a plurality of white-light LEDs 15a, which serve as a photographing light source and emit light having wavelengths of the entire visible light range, and a plurality of near-infrared-light LEDs 15b, which serve as an observation light source and emit near-infrared light whose intensity is peaked at a wavelength close to 850 nm. The plural white-light LEDs 15a and the plural near-infrared-light LEDs 15b are arranged at uniform intervals along the ring-shaped opening of the pupil stop 14 so that each of the white-light LEDs 15a is alternately adjacent to an associated one of the near-infrared-light LEDs 15b. Switching is performed between a group of the white-light LEDs 15a and a group of the near-infrared-light LEDs 15b so as to select one of the observation light source and the photographing light source. Thus, a fundus of a subject's eye E can efficiently be illuminated. In addition, a uniform illuminance distribution on a fundus surface can be obtained. Consequently, a high-picture-quality image of a fundus appropriately illuminated can be observed and photographed.

Thus, the LED illumination light source unit 15 serves as both an observation light source and a photographing light source. Consequently, a mechanism for inserting and removing wavelength selecting filters into or from the optical path of the illumination optical system is unnecessary. Accordingly, the illumination optical system can be miniaturized and simplified.

As need arises, a diffusion plate, such as a frosted glass plate, can be disposed in front of the LED illumination light source unit 15 in order to diffuse illumination light emitted by the white-light LEDs 15a or the near-infrared-light LEDs 15b, to reduce illumination unevenness, and to provide uniform illumination on the fundus of a subject's eye. Additionally, various wavelength selecting filters, such as an ultraviolet (UV) cut-off filter, can be disposed in front of the LED illumination light source unit 15 so as to select a range of wavelengths of light emitted from the LED illumination light source unit 15.

The LED illumination light source unit 15 can selectively emit white light, which is visible light needed to photograph a fundus of a subject's eye, or near-infrared light, which is needed to observe the fundus thereof, under the control of the power supply circuit 20. When the observation light amount adjusting knob 23 provided on the operation panel 22 is turned, the control unit 21 adjusts the amount of electric power supplied from the power supply circuit 20. The control unit 21 controls the amount of light to be emitted from the near-infrared-light LEDs 15b.

Near-infrared light emitted from the near-infrared-light LEDs 15b passes through the opening of the pupil stop 14 and that of the crystalline lens stop 13. Then, the near-infrared light is reflected by the mirror 12. Subsequently, the reflected near-infrared light is incident on a periphery of the perforated mirror 2 through the relay lens 11, the black point plate 10, the relay lens 9, and the cornea stop 8. The near-infrared light reflected by the periphery of the perforated mirror 2 uniformly irradiates the fundus of the subject's eye E through the objective lens 1. Then, reflection light reflected by the fundus of the subject's eye E is incident on the flip-up mirror 6 through the opening of the perforated mirror 2, the photographing stop 3, the focus lens 4, and the imaging lens 5. Subsequently, the reflection light reflected by the flip-up mirror 6 is incident on the image sensor 19 though the reflection mirror 16, the field lens 17, and the relay lens 18. Thus, an image of the fundus illuminated with the near-infrared light can be observed using a monitor (not illustrated).

An examiner performs alignment and focus adjustment while observing an image of the fundus of a subject's eye displayed on the monitor. Subsequently, when the examiner presses the photographing switch 25 of the operation panel 22, a photographing operation is performed. More specifically, the control unit 21 stops supply of electric power to the near-infrared-light LEDs 15b through the power supply circuit 20. Simultaneously, the control unit 21 causes the flip-up mirror 6 to retract out of the optical path. Next, the control unit 21 causes the power supply circuit 20 to supply electric power to the white-light LEDs 15a. Thus, the white-light LEDs 15a emit photographing visible light. The fundus of the subject's eye E is illuminated with visible light that is emitted from the white-light LEDs 15a and that passes through the same path as that through which near-infrared light emitted from the near-infrared-light LEDs 15b passes. Reflection light reflected by the fundus of the subject's eye E is incident on the imaging unit 7 through the opening of the perforated mirror 2, the photographic stop 3, the focus lens 4, and the imaging lens 5. The control unit 21 drives the imaging unit 7 in synchronization with emission of light from the white-light LEDs 15a. Thus, an image of the fundus of the subject's eye E illuminated with visible light is photographed and recorded.

Generally, photographing illumination is performed on a fundus of a subject's eye E in a short time period of 1/30 seconds or less in order to minimize influence of motion of the fundus of the subject's eye E. Therefore, the intensity of photographing light required is greater than that of the observation light. Accordingly, as illustrated in FIG. 4, additional white-light LEDs 15a serving as a photographing illumination light source can be provided so that the number of the white-light LEDs 15a is larger than that of the near-infrared-light LEDs 15b serving as an observation light source, so as to obtain a larger amount of visible light serving as the photographing light.

Figure 4:
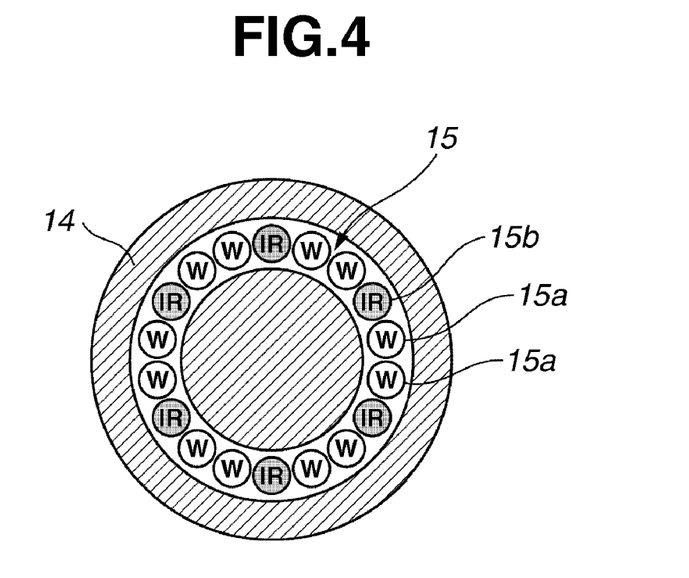
FIG. 4 illustrates another exemplary arrangement of LED light emitting elements according to the first exemplary embodiment of the present invention.

Each of ophthalmologic photographing apparatuses including LED light emitting elements arranged as illustrated in FIGS. 3 and 4 uses two types of LEDs, i.e., the white-light LEDs 15a and the near-infrared-light LEDs 15b. However, three or more types of LEDs can be used in an ophthalmologic photographing apparatus according to an exemplary embodiment of the present invention.

Figure 5:
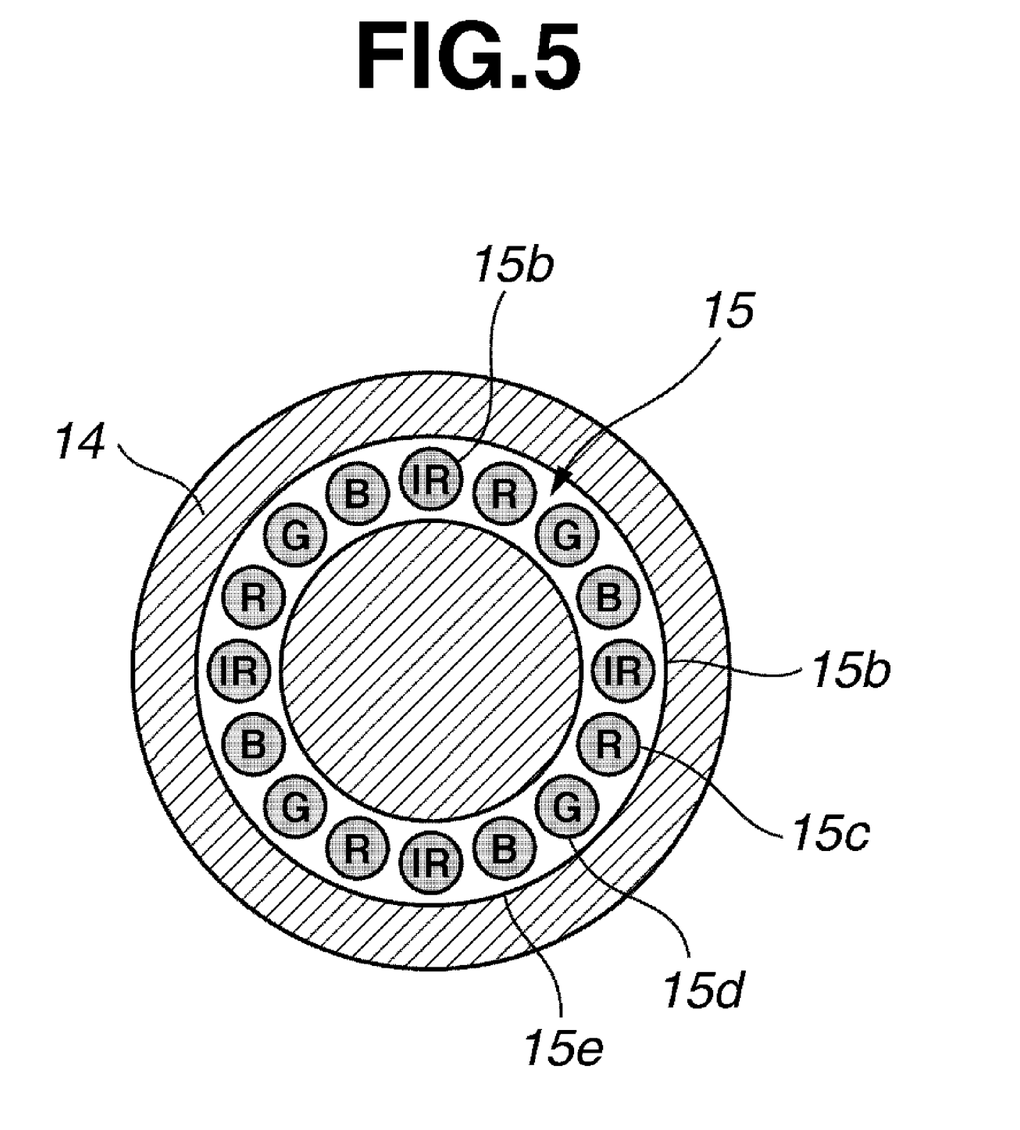
FIG. 5 illustrates a further exemplary arrangement of LED light emitting elements according to the first exemplary embodiment of the present invention.

FIG. 5 illustrates a further exemplary arrangement of LED light emitting elements according to the first exemplary embodiment of the present invention. More particularly, this exemplary embodiment uses RGB LEDs 15c, 15d, and 15e, which emit RGB light, instead of the white-light LEDs 15a. The RGB LEDs include red-light LEDs 15c, green-light LEDs 15d, and blue-light LEDs 15e. This exemplary embodiment also uses the near-infrared-light LEDs 15b. Even in this case, the LEDs of each of types 15b through 15e are arranged at uniform intervals. In addition, as illustrated in FIG. 5, the LEDs of the types 15b through 15e are provided in units of a set of sequentially arranged LEDs of the types 15b through 15e by repeatedly arranging this set of LEDs along the opening of the pupil stop 14. This set of LEDs is, e.g., a set of one near-infrared light LED 15b, one red light LED 15c, one green light LED 15d, and one blue light LED 15e, which are sequentially arranged in this order along the ring-shaped opening of the pupil stop 14. In the present example, an equal number of LEDs of each type is provided. Consequently, this exemplary embodiment can provide uniform illumination light, with which a fundus of a subject's eye is uniformly illuminated, thereby preventing occurrence of illuminance unevenness on a fundus surface thereof.

Thus, according to the present exemplary embodiment, the white-light LEDs 15a (or the RGB LEDs 15c through 15e) and the near-infrared-light LEDs 15b are concentrically disposed at uniform intervals along an annulus. Consequently, switching between observation light illumination and photographing light illumination can be performed by the single LED illumination light source unit 15. Thus, an optical member for switching therebetween is unnecessary. Consequently, the illumination optical system can be miniaturized and simplified. In addition, both observation light and photographing light can provide uniform luminance distributions on a fundus surface. Accordingly, a high-picture-quality fundus image can be observed and photographed.

Second Exemplary Embodiment

Figure 6:
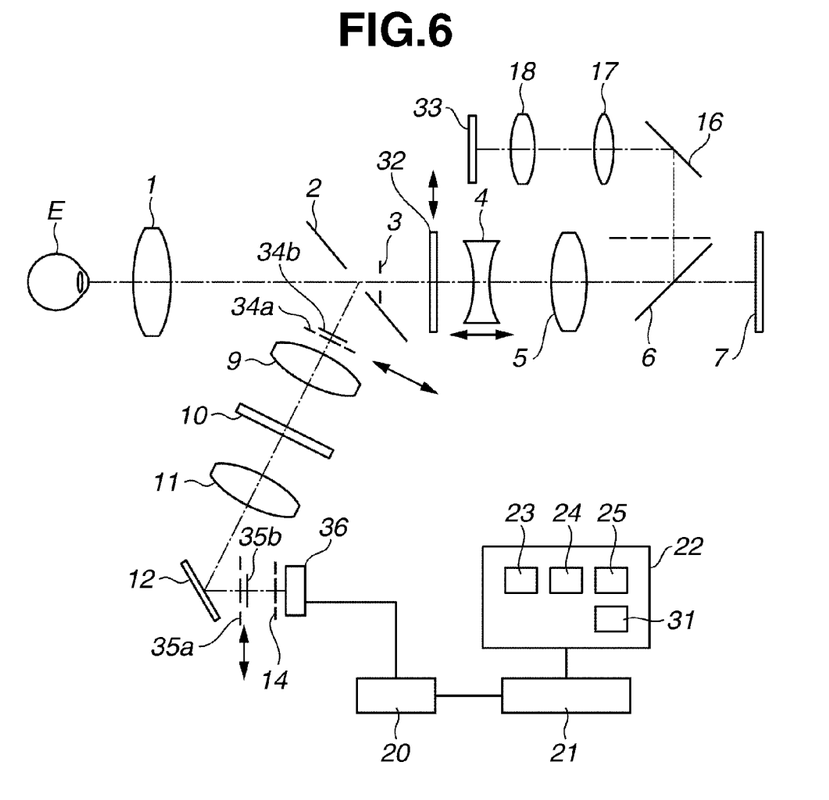
FIG. 6 illustrates a configuration of a fundus camera according to a second exemplary embodiment of the present invention.

FIG. 6 illustrates a configuration of a fluorescein fundus camera for diagnosis of blood vessels on a fundus of a subject's eye according to a second exemplary embodiment of the present invention. In FIG. 6, a member that is similar to an associated member of the non-mydriatic fundus camera according to the first exemplary embodiment is designated with the same reference numeral as that designating the associated member of the non-mydriatic fundus camera.

The fluorescein fundus camera according to the second exemplary embodiment of the present invention includes a photographing mode selector switch 31 provided on an operation panel 22 so as to select a photographing mode from among a fluorescent photographing mode and a color photographing mode. A barrier filter 32 having a transmission band of wavelengths ranging from 530 nm to 630 nm is provided between a photographic stop 3 and a focus lens 4 to be able to be inserted into and removed from the optical path of the illumination optical system. In the fluorescent photographing mode, the barrier filter 32 is inserted into the optical path by a mechanism (not illustrated) for inserting and removing the barrier filter 32. The fluorescein fundus camera further includes an image sensor 33, which is sensitive to visible light serving as color observation and fluorescent observation of a fundus of a subject's eye, instead of the image sensor 19, which is sensitive to near-infrared light according to the first exemplary embodiment of the present invention.

Additionally, a cornea stop 34a and a cornea baffle 34b, which can be inserted into and removed from the illumination optical path, are disposed on the optical path, instead of the cornea stop 8. A crystalline lens stop 35a and a crystalline lens baffle 35b, which can be inserted into and removed from the illumination optical path, are provided on the optical path, instead of the crystalline lens stop 13. An LED illumination light source unit 36 serving as an illumination light source is disposed in front of a pupil stop 14 having a ring-shaped opening. The LED illumination light source unit 36 includes white-light LEDs and blue-green-light LEDs, which emit blue-green light having wavelengths ranging from about 470 nm to about 500 nm, which is suited for fluorescent excitation.

In a fluorescent fundus examination, a fluorescent dye is injected into an arm of a subject. When a fluorescent agent flows into blood vessels of the fundus of the subject's eye, the blood vessels are illuminated with excitation light having an excitation wavelength of the fluorescent agent. Excited fluorescent light is separated from the excitation light by the barrier filter 32, so that the fluorescent light is photographed. In the fluorescent fundus examination using fluorescein, which is a typical fluorescent agent, a fundus of a subject's eye is illuminated with excitation light having a wavelength close to 500 nm. Fluorescent light is photographed by cutting off excitation light using the barrier filter 32 having a transmission range of wavelengths ranging from about 530 nm to about 630 nm.

The LED illumination light source unit 36 can selectively emit visible light for color observation and color photographing, and can also emit blue-green excitation light needed for fluorescent observation and fluorescent photographing. The LED illumination light source unit 36 can be used as both an observation light source and a photographing light source. In addition, the LED illumination light source unit 36 can use both visible light and fluorescent excitation illumination light. An exciter filter for selecting a wavelength of excitation light, and a moving part, such as a mechanism for inserting and removing the exciter filter, are unnecessary. Consequently, the illumination optical system can be miniaturized and simplified.

Figure 7:
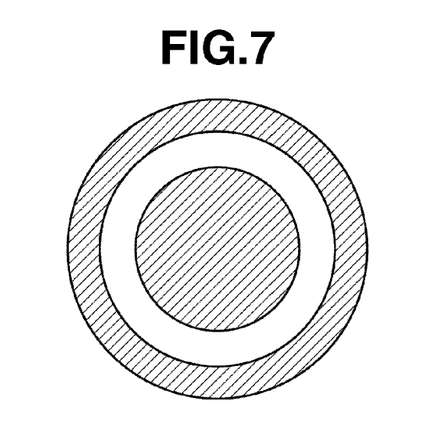
FIG. 7 illustrates an exemplary ring-shaped opening for color photographing according to the second exemplary embodiment of the present invention.

The necessary shape of the ring-shaped opening depends on the photographing mode. FIG. 7 illustrates an exemplary ring-shaped opening in a surface of a pupil stop for a color photographing mode when the cornea baffle 34b and the crystalline baffle 35b are inserted into the optical path. During color photographing, the cornea baffle 34b and the crystalline baffle 35b are inserted into the optical path, and a central shielding part of the ring-shaped opening is formed to be large so that harmful light coming from the cornea or the crystalline lens of a subject's eye E is prevented from being incident on the opening.

Figure 8:
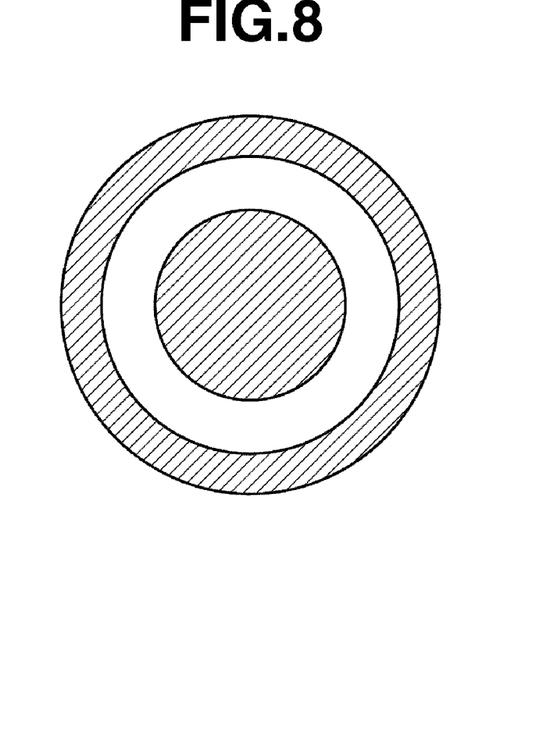
FIG. 8 illustrates another exemplary ring-shaped opening for fluorescent photographing according to the second exemplary embodiment of the present invention.

FIG. 8 illustrates an exemplary ring-shaped opening of a pupil stop that is used for fluorescent photographing when the cornea baffle 34b and the crystalline baffle 35b are retracted from the optical path. At fluorescent photographing, most of reflection light reflected from a cornea and a crystalline lens of a subject's eye E is cut off by the barrier filter 32. Thus, the central shielding part of the ring-shaped opening for preventing harmful reflection light from being incident thereon can be small, as compared with that at color photographing. Accordingly, the cornea baffle 34b and the crystalline baffle 35b are retracted from the optical path, so that fluorescent light is photographed in a state in which a large amount of illumination light is supplied to the fundus of the subject's eye E.

Figure 9:
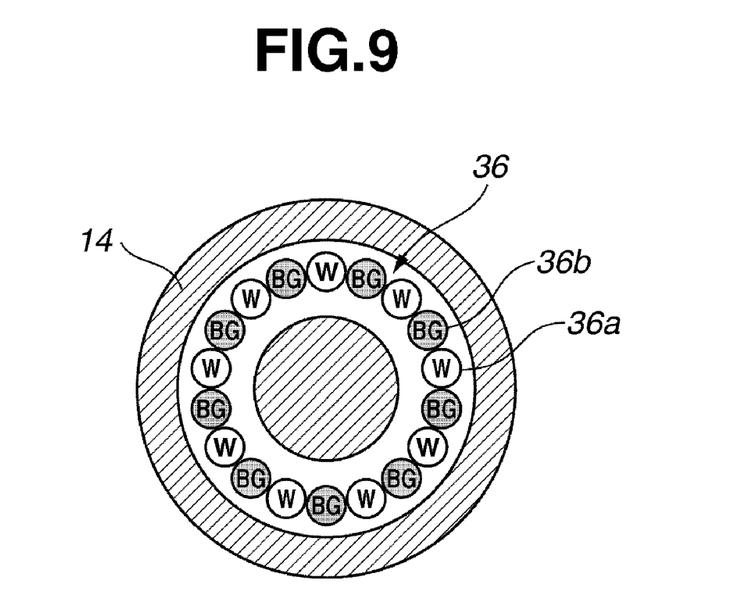
FIG. 9 illustrates an exemplary arrangement of LED light emitting elements according to the second exemplary embodiment of the present invention.

FIG. 9 illustrates an exemplary arrangement of LED light emitting elements of the LED illumination light source unit 36. The LED light emitting elements include a group of white-light LEDs 36a and that of blue-green-light LEDs 36b for fluorescent excitation. The LEDs of each of these groups are arranged at uniform intervals along the opening of the pupil stop 14 so that each of the plural white-light LEDs 36a is alternately adjacent to an associated one of the plural blue-green-light LEDs 36b. That is, the LEDs of each of these groups are arranged at uniform intervals, so that a uniform illuminance distribution on a fundus surface can be obtained, and that a high-picture-quality image of a fundus of a subject's eye appropriately illuminated can be observed and photographed. In other words, LEDs of each type are spaced at substantially equal angular intervals about the optical axis.

Figure 10:
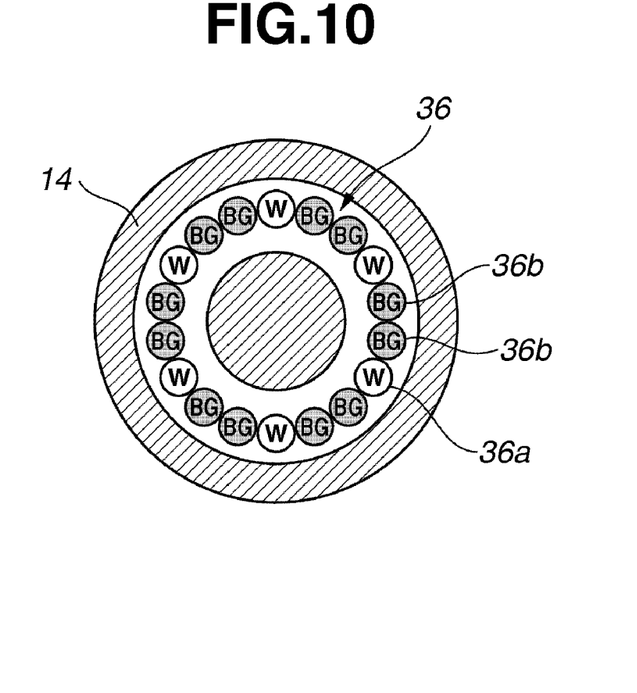
FIG. 10 illustrates another exemplary arrangement of LED light emitting elements according to the second exemplary embodiment of the present invention.

In view of the fact that a larger amount of light is needed for fluorescent excitation, the blue-green-light LEDs 36b can be provided so that the number of the blue-green-light LEDs 36b is larger than that of the white-light LEDs 36a, as illustrated in FIG. 10. In consideration of an amount and directivity of light emitted from each of the LED light emitting elements, the number of blue-green-light LEDs 36b and that of white-light LEDs 36a can be changed.

Figure 11:
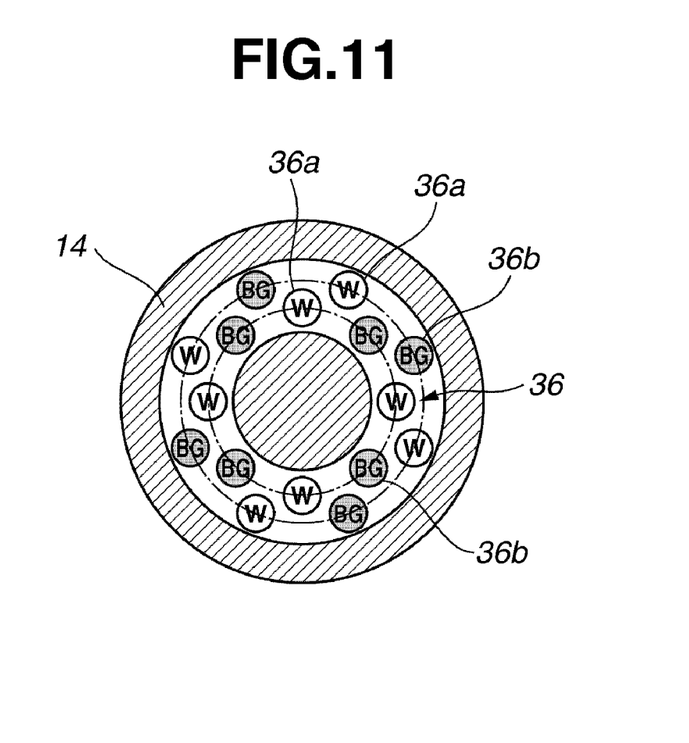
FIG. 11 illustrates a further exemplary arrangement of LED light emitting elements according to the second exemplary embodiment of the present invention.

The LED light emitting elements do not necessarily have to be arranged on the same circle. The LED light emitting elements can be concentrically arranged, as illustrated in FIG. 11. Such a concentric arrangement of the LED light emitting elements achieves an effect that a fundus of a subject's eye can be uniformly illuminated even in a case where the ring-shaped opening has a large width. Once again, LEDs of each type are spaced at substantially equal angular intervals about the optical axis.

Figure 12:
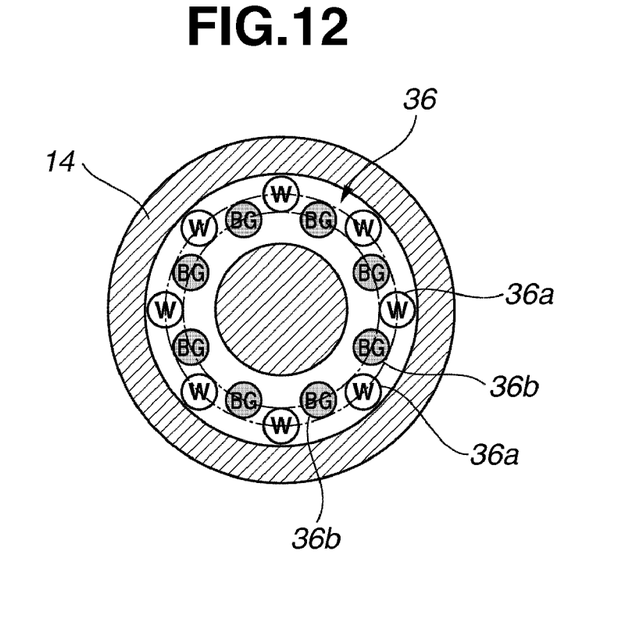
FIG. 12 illustrates yet another exemplary arrangement of LED light emitting elements according to the second exemplary embodiment of the present invention.

As described above, the ring-shaped opening for color photographing, which is illustrated in FIG. 7, differs in shape from the ring-shaped opening for fluorescent photographing, which is illustrated in FIG. 8. Consequently, each of the ring-shaped openings can efficiently be illuminated by setting the arrangement of the LEDs according to the size (or shape) of each of these ring-shaped openings. The LED light emitting elements of each of the groups, i.e., the group of the white-light LEDs 36a and the group of the blue-green-light LEDs 36b can be concentrically arranged, as illustrated in FIG. 12. Thus, the ring-shaped openings respectively corresponding to the photographing modes can be uniformly and efficiently illuminated. Once again, LEDs of each type are spaced at substantially equal angular intervals about the optical axis.

Figure 13:
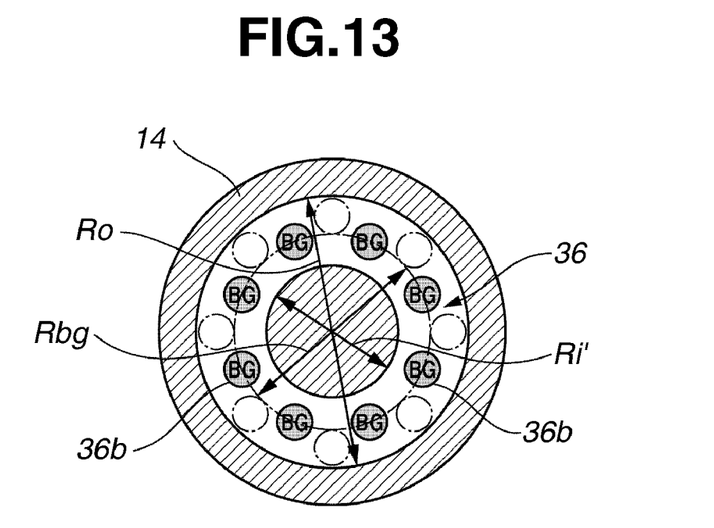
FIG. 13 also illustrates an exemplary arrangement of LED light emitting elements according to the second exemplary embodiment of the present invention.

FIG. 13 illustrates an exemplary ring-shaped opening formed corresponding to fluorescent photographing and also illustrates an exemplary arrangement of the blue-green-light LEDs 36b. During fluorescent photographing, the cornea baffle 34b and the crystalline lens baffle 35b are retracted from the optical path. Thus, the cornea baffle 34b and the crystalline lens baffle 35b act as a small baffle. The blue-green-light LEDs 36b are disposed at the center of the opening so that the opening is uniformly illuminated. In this case, the blue-green-light LEDs 36b are arranged so that a radius Rbg of the arrangement of the blue-green-light LEDs 36b is given by the following equation:

$$Rbg=(1/2)(Ro+Ri')$$

where "Ro" designates an outside diameter of the ring-shaped opening, and "Ri'" denotes an inside diameter (i.e., a small baffle diameter) of the ring-shaped opening. That is, the radius Rbg of the arrangement of the blue-green-light LEDs 36b has a value equal to an average value of the outside diameter Ro and the inside diameter Ri' of the ring-shaped opening.

Figure 14:
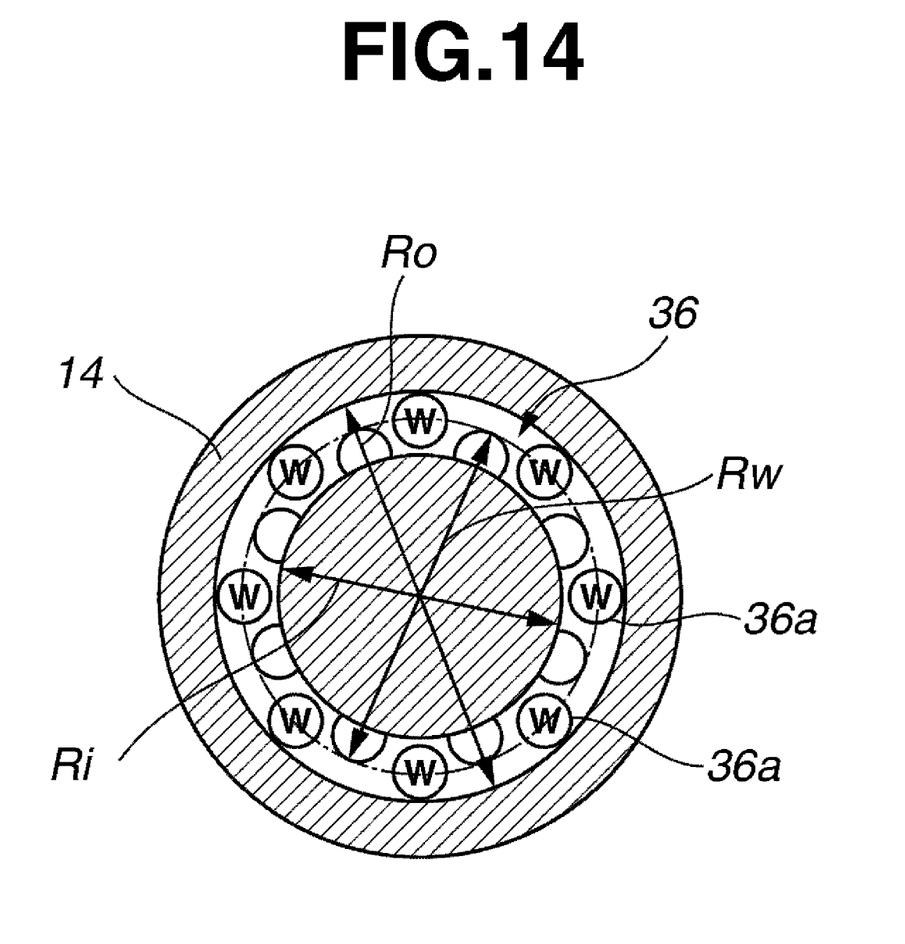
FIG. 14 illustrates a last exemplary arrangement of LED light emitting elements according to the second exemplary embodiment of the present invention.

FIG. 14 illustrates a ring-shaped opening during color photographing and an exemplary arrangement of white-light LEDs 36a. During color photographing, the cornea baffle 34b and the crystalline baffle 35b are inserted into the optical path. Thus, the cornea baffle 34b and the crystalline lens baffle 35b act as a large baffle. The white-light LEDs 36a are disposed at the center of the opening so that the opening can uniformly be illuminated. That is, the white-light LEDs 36a are arranged so that a radius Rw of the arrangement of the white-light LEDs 36a is given by the following equation:

$$Rw=(1/2)(Ro+Ri)$$

where "Ro" designates an outside diameter of the ring-shaped opening, and "Ri" denotes an inside diameter (i.e., a large baffle diameter) of the ring-shaped opening.

At that time, $Ri > Ri'$. Thus, $Rw > Rbg$. Consequently, the white-light LEDs 36a are disposed on the outer side of the blue-green-light LEDs 36b. Such an arrangement of the LED light emitting elements of the light source achieves a more uniform luminance distribution on a cross-section of the ring-shaped opening corresponding to each of the photographing modes. Consequently, a high-picture-quality image of a fundus of a subject's eye can be observed and photographed.

Thus, a single LED illumination light source unit 36 can perform both observation light illumination and photographing light illumination by concentrically disposing a plurality of white-light LEDs 36a and a plurality of blue-green-light LEDs 36b on circles having different radii, respectively. Consequently, a separate optical member for switching between observation light illumination and photographing light illumination is unnecessary. Accordingly, the illumination optical system can be miniaturized and simplified. In addition, both observation light and photographing light can provide uniform luminance distributions on a cross-section of the ring-shaped opening. Thus, a high-picture-quality fundus image can be observed and photographed.

According to the present exemplary embodiment, LED light emitting elements configured to emit light having necessary wavelengths are arranged close to the center of respective ring-shaped openings corresponding to different photographing modes, such as a fluorescent photographing mode and a color photographing mode. Thus, a fundus of a subject's eye can efficiently be illuminated. Consequently, an exciter filter for wavelength separation of excitation light and a mechanism for inserting and removing the exciter filter are unnecessary. Accordingly, the illumination optical system can be miniaturized and simplified. The ophthalmologic photographing apparatus according to an exemplary embodiment of the present invention can efficiently and uniformly illuminate a fundus of a subject's eye with a simple structure by using a single compound light source as both an observation light source and a photographing light source.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2007-052596 filed Mar. 2, 2007, which is hereby incorporated by reference herein in its entirety.

What is claimed is:

1. An ophthalmologic photographing apparatus comprising:
   a light source having two types of light-emitting-diodes (LED) light emitting elements configured to emit light of different wavelengths, wherein two types of LED is concentrically arranged;
   an illumination optical system configured to illuminate a fundus of a subject's eye with light emitted by the light source;
   a plurality of aperture stops having an opening of a different size;
   an imaging optical system configured to form a fundus image from light reflected from the fundus of the subject's eye illuminated by the illumination optical system; and
   a control unit configured to select and turn on one of the two types of LED light emitting elements and to insert the plurality of aperture stops into an optical path of the illumination optical system according to a selected type of LED light;
   characterized in that two types of LEDs are arranged at corresponding openings different from each other.

2. The ophthalmologic photographing apparatus according to claim 1, wherein the control unit selects and turns on one of the two types of LED light emitting elements.

3. The ophthalmic photographic apparatus according to claim 1, wherein the two types of LED light emitting elements include blue-green-light LEDs configured to excite a fluorescent agent in a fundus of a subject's eye, and white-light LEDs, and blue-green-light LEDs are arranged at a small baffle diameter in relation to the white-light LEDs.

* * * * *